(12) United States Patent
Li et al.

(10) Patent No.: US 10,611,742 B2
(45) Date of Patent: Apr. 7, 2020

(54) 4-OXO-4,5-DIHYDROTHIAZOLE DERIVATIVE, PREPARATION METHOD AND USE THEREOF

(71) Applicant: Institute of Pharmacology and Toxicology Academy of Military Medical Sciences P.L.A. China, Beijing (CN)

(72) Inventors: Song Li, Beijing (CN); Junhai Xiao, Beijing (CN); Libao Xu, Beijing (CN); Ruiyuan Cao, Beijing (CN); Fangyuan Cao, Beijing (CN); Hongliang Wang, Beijing (CN); Wu Zhong, Beijing (CN); Zhibing Zheng, Beijing (CN); Yunde Xie, Beijing (CN); Xingzhou Li, Beijing (CN); Xinbo Zhou, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/777,774

(22) PCT Filed: Nov. 24, 2016

(86) PCT No.: PCT/CN2016/107023
§ 371 (c)(1),
(2) Date: May 21, 2018

(87) PCT Pub. No.: WO2017/088776
PCT Pub. Date: Jun. 1, 2017

(65) Prior Publication Data
US 2018/0370928 A1 Dec. 27, 2018

(30) Foreign Application Priority Data
Nov. 27, 2015 (CN) .......................... 2015 1 0846380

(51) Int. Cl.
*C07D 277/52* (2006.01)
*A61P 31/14* (2006.01)
*C07D 277/54* (2006.01)

(52) U.S. Cl.
CPC ............ *C07D 277/54* (2013.01); *A61P 31/14* (2018.01); *C07D 277/52* (2013.01); *Y02A 50/465* (2018.01)

(58) Field of Classification Search
CPC .................................................. C07D 277/54
See application file for complete search history.

(56) References Cited

FOREIGN PATENT DOCUMENTS

CN 102584809 A 7/2012
WO WO 2013/010218 A1 1/2013

OTHER PUBLICATIONS

WebMD. Lung Disease Overview. (2018) Web < https://www.webmd.com/lung/lung-diseases-overview#1>.*
UCSF Medical Center. Neurological Disorders. (2016) Web: <https://www.ucsfhealth.org/conditions/neurological_disorders/>.*
MedlinePlus. Auto-immune Diseases: MedlinePlus. (2014). Web: <https://www.nlm.nih.gov/medlineplus/autoimmunediseases.html>.*
Singh, Sunita. J. Clin. Microbiol. (2002) 2823-2827.*
Extended European Search Report, including the supplementary European search report and the European search opinion, for EP Appl. No. 16867999.1, dated Apr. 8, 2019, European Patent Office, Munich, Germany.
Robertson, MJ et al., "5-Aryl-2-(naphtha-1-yl)sulfonamido-thiazol-4(5H)-ones as clathrin inhibitors," Org Biomol Chem. Nov. 29, 2016;14(47):11266-11278.
International Search Report (ISR) for PCT/CN2016/107023; I.A. fd: Nov. 24, 2016; dated Feb. 22, 2017, State Intellectual Property Office of the P.R. China, Beijing, China.
International Preliminary Report on Patentability (IPRP) (Chapter I of the Patent Cooperation Treaty) (PCT Rule 44*bis*) for PCT/CN2016/107023; I.A. fd: Nov. 24, 2016; dated May 29, 2018, by The International Bureau of WIPO, Geneva, Switzerland.
Stahlschmidt, W. et al., "Clathrin terminal domain-ligand interactions regulate sorting of mannose 6-phosphate receptors mediated by AP-1 and GGA adaptors," J Biol Chem. Feb. 21, 2014;289(8):4906-18. doi: 10.1074/jbc.M113.535211. Epub Jan. 9, 2014, Am. Soc. for Biochem. and Molec. Biol., Baltimore, MD.

(Continued)

*Primary Examiner* — Emily A Bernhardt
*Assistant Examiner* — Laura M Daniel
(74) *Attorney, Agent, or Firm* — Sterne, Kessler, Goldstein & Fox P.L.L.C.

(57) ABSTRACT

The present invention relates to a compound represented by Formula I, a racemate or optical isomer thereof, or a pharmaceutically acceptable salt, a solvate or a hydrate thereof, a pharmaceutical composition comprising the compound, and a use thereof in the manufacture of a medicament for preventing and/or treating a disease or disorder associated with a viral infection.

13 Claims, No Drawings

(56) References Cited

OTHER PUBLICATIONS

Robertson, MJ et al., "Synthesis of the Pitstop family of clathrin inhibitors," Nat Protoc. Jul. 2014;9(7):1592-606. doi: 10.1038/nprot.2014.106. Epub Jun. 12, 2014, Nature Pub. Group, London, UK.
First Office Action for CN Appl. No. 201510846380.5, dated Oct. 25, 2018, including Search Report dated Oct. 19, 2018, mailed from CNIPA, Beijing, CN.
Search report dated Oct. 19, 2018 for CN Appl. No. 201510846380.5, mailed from CNIPA, Beijing, CN.

* cited by examiner

4-OXO-4,5-DIHYDROTHIAZOLE DERIVATIVE, PREPARATION METHOD AND USE THEREOF

TECHNICAL FIELD

The present invention belongs to a medical and chemical engineering field, relates to a novel broad-spectrum agent against viral infection and use thereof in the manufacture of a medicament for preventing and/or treating viral diseases caused by various viruses.

BACKGROUND ART

Since Martinus Willem Beijerinck proposed the word "virus" for the first time in 1899, more than 6,000 viruses have been identified over the world. Among them, human immunodeficiency virus, hepacivirus, influenza virus, severe acute respiratory syndrome (SARS) virus, enterovirus EV71, and Ebola virus which outbreaks in West African countries with a high lethality, have become natural enemies to human health. Viruses can cause an immense damage even in the early stage of epidemics, including personal injury, social panic, and economic fluctuation, etc., and therefore have a serious impact on the national economy and social stability. In this case, even drugs with a weak therapeutic effect will have an inestimable effect on reducing personal injury, especially eliminating social panic and stabilizing economic fluctuation. The optimum option for reducing the hazards of this new public health emergency is to develop broad-spectrum antiviral agents.

Virus reproduction will not happen in the absence of host cells. Entry of most of viruses into host cells occur mainly via Clathrin-mediated endocytosis (CME), Caveolin-mediated endocytosis, Clathrin and Caveolin-independent endocytosis and Macropinocytosis. Entry of a lot of viruses such as enterovirus EV71, Dengue virus, and Hepatitis C virus into cells occurs mainly via CME. CME is a potential target for broad-spectrum anti-virus in recent years, since its function and mechanism are independent of viruses themselves, and drug resistance does not occur easily with virus variation.

In CME, clathrin, adaptor protein (AP-2), dynamin, and the like, are essential key molecules. The mechanism concerning entry of a virus into a cell via Clathrin-mediated endocytosis has been well studied, and the whole endocytosis process can be divided into the following four stages generally.

1) Nucleation of clathrin-coated pits: in this stage, it is dependent on the participation of a protein complex of FCHo1/2, eps15 and intersectin-1. This complex assembles at coated pit nuclear sites prior to clathrin coat formation and recruits the AP-2 adaptor protein via the multiple AP-2 binding sites of eps15. Clathrin is then recruited to the surface of cytoplasmic membrane by AP-2, and the increased local clathrin concentration exceeds the threshold required for polymerization of the clathrin triskelion, which allows for local assembly of clathrin coat. Clathrin is necessary in stabilizing the shape of coated pits and driving membrane invagination.

2) Cargo capture in coated pits: a virus as cargo is bound to a specific receptor that recognizes the virus on the surface of cell membrane and therefore is captured and detained. The formation of the clathrin network activates Adaptin-associated kinase 1 (AAK1), which phosphorylates the μ2-subunit of AP-2 thereby AP-2 is bound more strongly to phosphatidylinositol diphosphate ($PIP_2$) of membrane to expose the μ2 cargo-binding site. The cargo-AP-2 complex simulates the activity of can activate PIP kinase type Iγ (PIPK Iγ), and contributes to the increase in the $PIP_2$ concentration of coated membrane zone, thus contributes to appearance of sufficient sites to which AP-2, epsin and other CME-associated proteins are bound, which maintains the growth of clathrin-coated pits (CCPs).

3) Curvature induction and membrane invagination: the initial membrane deformation may occur during clathrin-coated pit (CCP) nucleation, where FCHo proteins make a small curvature of membrane through their F-BAR domains. The occurrence of this curvature is putatively mediated through coating of multiple membrane-binding proteins and clathrin, including epsin and amphiphysin, etc. The membrane curvature around the coat forms a growing bud on the cell membrane surface. As the membrane invaginates and buds into a vesicle, a tubular neck region begins to form on the membrane surface, this region has not free $PIP_2$ coated by and contained in clathrin, but has still a high curvature, which attracts proteins containing curvature-sensing N-BAR domains.

4) Vesicle scission and uncoating: once clathrin-coated vesicles have a sufficiently high curvature, dynamin is capable of forming a ring structure around the vesicle neck, and an inward compression force is generated by GTP hydrolysis-triggering mechanism, and vesicle scission is carried out with the participation of proteins such as amphiphysin, and the scissored vesicles are uncoated immediately. The uncoating mechanism may be as follows, in the initial stage, endophilin recruits the synaptojanin with phosphatase activity to the vesicles, thereby disrupting the high affinity between AP-2 and $PIP_2$, resulting in the conversion of $PIP_2$ to PI(4)P. GAK/auxilin bind the newly formed PI(4)P via a PTEN-like domain and recruit the Hsc70 chaperone to the coated vesicle to interact with AP-2 and clathrin, thus the uncoating process is completed. The uncoated vesicles are polymerized or fused to endosomes directly, followed by fusion to lysosomes, the contents are degraded, membrane receptors are separated from virus ligands, and the entire entry of a virus into a cell is finished.

Therefore, the inhibition of clathrin may function to block the endocytosis of a virus. The purpose of the present invention is to synthesize new clathrin inhibitors for use in the preparation of broad-spectrum antiviral agents for preventing and/or treating viral diseases caused by various viruses.

CONTENTS OF INVENTION

In the first aspect, the present invention relates to a compound represented by Formula I, a racemate or an optical isomer thereof, or a pharmaceutically acceptable salt, a solvate or a hydrate thereof,

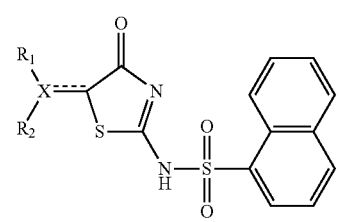

I wherein,

X is a C or N atom;

≡≡≡ represents a single bond or a double bond;

$R_1$ and $R_2$ each are independently hydrogen or phenyl ring, wherein the phenyl ring is optionally substituted with 1, 2, 3, 4 or 5 identical or different $R_3$, each $R_3$ is independently selected from the group consisting of: hydrogen, halogen, hydroxyl, alkyl, haloalkyl, alkoxy, amino, amino monosubstituted or disubstituted with alkyl, carboxyl, acylamino, and phenyl, when X is a C atom, ≡≡≡ represents a double bond, $R_1$ is a hydrogen, and the phenyl ring is monosubstituted with $R_3$ at position 4, $R_3$ is not a bromine atom.

In a preferred embodiment of the present invention, in the compound of Formula I, a racemate or an optical isomer thereof, or a pharmaceutically acceptable salt, a solvate or a hydrate thereof according to the present invention, $R_1$ and $R_2$ are not simultaneously hydrogen.

In a preferred embodiment of the present invention, the compound of Formula I, a racemate or an optical isomer thereof, or a pharmaceutically acceptable salt, a solvate or a hydrate thereof according to the present invention, or any of the above applicable embodiments, may be a compound of Formula Ia,

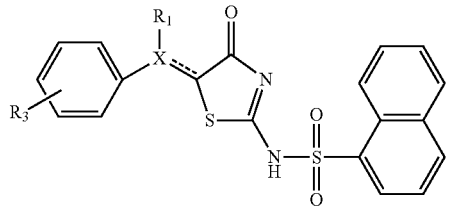

Ia wherein,

X is a C or N atom;

≡≡≡ represents a single bond or a double bond;

$R_1$ is a hydrogen or a phenyl ring, wherein the phenyl ring is optionally substituted with 1, 2, 3 or 4 identical or different $R_3$, each $R_3$ is independently selected from the group consisting of: hydrogen, halogen, hydroxyl, $C_{1-8}$ alkyl, $C_{1-8}$ haloalkyl, $C_{1-8}$ alkoxy, amino, amino monosubstituted or disubstituted with $C_{1-8}$alkyl, carboxyl, R'(C=O)NH—, and phenyl, wherein R' is $C_{1-8}$ alkyl, when X is a C atom, ≡≡≡ represents a double bond, $R_1$ is a hydrogen, and the phenyl ring is monosubstituted with $R_3$ at position 4, $R_3$ is not a bromine atom.

In a preferred embodiment of the present invention, the compound of Formula I according to the present invention may be a compound represented by Formula Ib, Formula Ic or Formula Id, or a racemate or an optical isomer thereof, or a pharmaceutically acceptable salt, a solvate or a hydrate thereof,

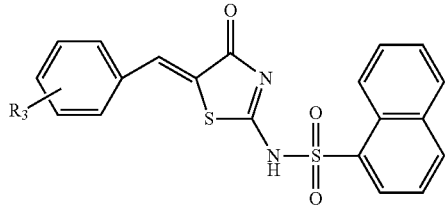

Ib

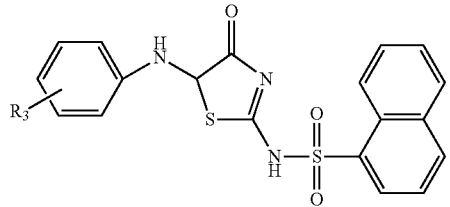

Ic

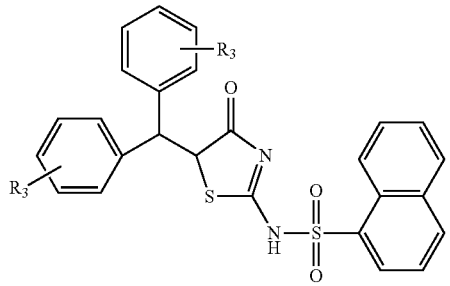

Id wherein, $R_3$ is absent or represents 1, 2, 3 or 4 identical or different substituents present on the phenyl ring, each $R_3$ is independently selected from the group consisting of: hydrogen, halogen, hydroxyl, $C_{1-8}$ alkyl, $C_{1-8}$ haloalkyl, $C_{1-8}$ alkoxy, amino, amino monosubstituted or disubstituted with $C_{1-8}$ alkyl, carboxyl, R'(C=O)NH—, and phenyl, wherein R' is $C_{1-8}$ alkyl, when the compound of Formula I is the compound of Formula Ib, or a racemate or an optical isomer thereof, or a pharmaceutically acceptable salt, a solvate or a hydrate thereof, and the phenyl ring in Formula Ib is monosubstituted with $R_3$ at position 4, $R_3$ is not a bromine atom.

In another preferred embodiment of the present invention, the compound of Formula I according to the present invention may be a compound of Formula Ib, or a racemate or an optical isomer thereof, or a pharmaceutically acceptable salt, a solvate or a hydrate thereof,

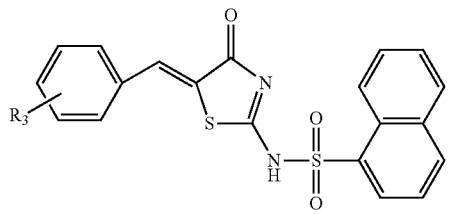

Ib wherein, $R_3$ is absent or represents 1, 2, 3 or 4 identical or different substituents present on the phenyl ring, each $R_3$ is independently selected from the group consisting of: hydrogen, halogen, hydroxyl, $C_{1-8}$ alkyl, $C_{1-8}$ haloalkyl, $C_{1-8}$ alkoxy, amino, amino monosubstituted or disubstituted with $C_{1-8}$ alkyl, carboxyl, R'(C=O)NH—, and phenyl, wherein R' is $C_{1-8}$ alkyl, moreover, when the phenyl ring is monosubstituted with $R_3$ at position 4, $R_3$ is not a bromine atom.

In another preferred embodiment of the present invention, the compound of Formula I according to the present invention may be a compound of Formula Ic, or a racemate or an optical isomer thereof, or a pharmaceutically acceptable salt, a solvate or a hydrate thereof, Ic

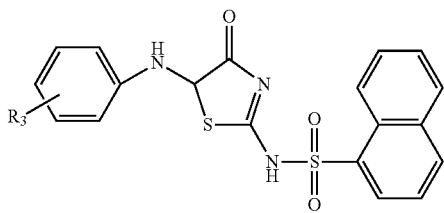

wherein, $R_3$ is absent or represents 1, 2, 3 or 4 identical or different substituents present on the phenyl ring, each $R_3$ is independently selected from the group consisting of: hydrogen, halogen, hydroxyl, $C_{1-8}$ alkyl, $C_{1-8}$ haloalkyl, $C_{1-8}$ alkoxy, amino, amino monosubstituted or disubstituted with $C_{1-8}$ alkyl, carboxyl, R'(C=O)NH—, and phenyl, wherein R' is $C_{1-8}$ alkyl.

In another preferred embodiment of the present invention, the compound of Formula I according to the present invention may be a compound of Formula Id, or a racemate or an optical isomer thereof, or a pharmaceutically acceptable salt, a solvate or a hydrate thereof, Id

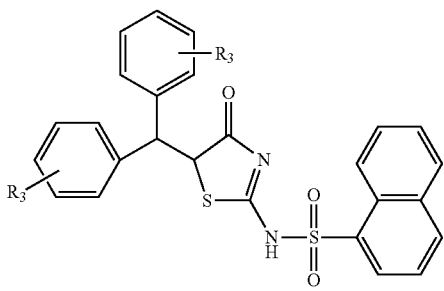

wherein, $R_3$ is absent or represents 1, 2, 3 or 4 identical or different substituents present on the phenyl ring, each $R_3$ is independently selected from the group consisting of: hydrogen, halogen, hydroxyl, $C_{1-8}$ alkyl, $C_{1-8}$ haloalkyl, $C_{1-8}$ alkoxy, amino, amino monosubstituted or disubstituted with $C_{1-8}$ alkyl, carboxyl, R'(C=O)NH—, and phenyl, wherein R' is $C_{1-8}$ alkyl.

In another preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is absent or represents 1 substituent present on the phenyl ring.

In another preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is absent or represents 2 identical or different substituents present on the phenyl ring.

In another preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, each $R_3$ is independently selected from the group consisting of: hydrogen, halogen, hydroxyl, $C_{1-6}$ alkyl, $C_{1-6}$ haloalkyl, $C_{1-6}$ alkoxy, amino, amino monosubstituted or disubstituted with $C_{1-6}$ alkyl, carboxyl, R'(C=O)NH— and phenyl, wherein R' is $C_{1-6}$ alkyl.

In another preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, each $R_3$ is independently selected from the group consisting of: hydrogen, halogen, hydroxyl, $C_{1-4}$ alkyl, $C_{1-4}$ haloalkyl, $C_{1-4}$ alkoxy, amino, amino monosubstituted or disubstituted with $C_{1-4}$ alkyl, carboxyl, R'(C=O)NH— and phenyl, wherein R' is $C_{1-4}$ alkyl.

In another preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, each $R_3$ is independently selected from the group consisting of: hydrogen, fluorine, chlorine, bromine, hydroxyl, methyl, ethyl, n-propyl, isopropyl, n-butyl, isobutyl, sec-butyl, tert-butyl, trifluoromethyl, methoxy, ethoxy, propoxy, amino, methylamino, dimethylamino, ethylamino, diethylamino, propylamino, carboxyl, $CH_3$(C=O)NH—, $C_2H_5$(C=O)NH— and phenyl.

In another preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, each $R_3$ is independently selected from the group consisting of: hydrogen, fluorine, chlorine, bromine, hydroxyl, methoxy, amino, diethylamino, propylamino, carboxyl, $CH_3$(C=O)NH— and phenyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is absent or represents 1, 2, or 3 identical or different substituents present on the phenyl ring, each $R_3$ is independently selected from the group consisting of: hydrogen, halogen, hydroxyl, $C_{1-6}$alkyl, $C_{1-6}$haloalkyl, $C_{1-6}$alkoxy, amino, amino monosubstituted or disubstituted with $C_{1-6}$alkyl, carboxyl, R'(C=O)NH— and phenyl, wherein R' is $C_{1-6}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is absent or represents 1 or 2 identical or different substituents present on the phenyl ring, each $R_3$ is independently selected from the group consisting of: hydrogen, halogen, hydroxyl, $C_{1-4}$alkyl, $C_{1-4}$haloalkyl, $C_{1-4}$alkoxy, amino, amino monosubstituted or disubstituted with $C_{1-4}$alkyl, carboxyl, R'(C=O)NH— and phenyl, wherein R' is $C_{1-4}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is absent or represents 1 or 2 identical or different substituents present on the phenyl ring, each $R_3$ is independently selected from the group consisting of: hydrogen, fluorine, chlorine, bromine, hydroxyl, methyl, ethyl, n-propyl, isopropyl, n-butyl, isobutyl, sec-butyl, tert-butyl, trifluoromethyl, methoxy, ethoxy, propoxy, amino, methylamino, dimethylamino, ethylamino, diethylamino, propylamino, carboxyl, $CH_3(C=O)NH-$, $C_2H_5(C=O)NH-$ and phenyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is absent or represents 1 or 2 identical or different substituents present on the phenyl ring, each $R_3$ is independently selected from the group consisting of: hydrogen, fluorine, chlorine, bromine, hydroxyl, methoxy, amino, diethylamino, propylamino, carboxyl, $CH_3(C=O)NH-$ and phenyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-8}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-8}$haloalkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-8}$alkoxy.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is amino monosubstituted or disubstituted with $C_{1-8}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $R'(C=O)NH-$, wherein $R'$ is $C_{1-8}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-6}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-6}$haloalkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-6}$alkoxy.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is amino monosubstituted or disubstituted with $C_{1-6}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $R'(C=O)NH-$, wherein $R'$ is $C_{1-6}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-4}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-4}$haloalkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $C_{1-4}$alkoxy.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is amino monosubstituted or disubstituted with $C_{1-4}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $R'(C=O)NH-$, wherein $R'$ is $C_{1-4}$alkyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is hydrogen.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is fluorine.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is chlorine.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is bromine.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is hydroxyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is methoxy.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is amino.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is diethylamino.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is propylamino.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is carboxyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is $CH_3(C=O)NH-$.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is phenyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is ethyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is propyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is n-propyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is isopropyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is n-butyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is isobutyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is sec-butyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is tert-butyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is trifluoromethyl.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is ethoxy.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is propoxy.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is dimethylamino.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is methylamino.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, $R_3$ is ethylamino.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, the phenyl ring is optionally monosubstituted with $R_3$ at position 3.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, the phenyl ring is optionally monosubstituted with $R_3$ at position 4.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, the phenyl ring is optionally monosubstituted with $R_3$ at position 2.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, the phenyl ring is optionally disubstituted with $R_3$ at positions 2 and 4.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, the phenyl ring is optionally disubstituted with $R_3$ at positions 3 and 4.

In a preferred embodiment of the present invention, in the compound of Formula I, Formula Ia, Formula Ib, Formula Ic or Formula Id, or a racemate or an optical isomer thereof, or a pharmaceutically acceptable salt, a solvate or a hydrate thereof, or in any of the above applicable embodiments, the phenyl ring is optionally disubstituted with $R_3$ at positions 2 and 6.

In another preferred embodiment of the present invention, in the compound of Formula Ib, or a racemate or an optical isomer thereof, or a pharmaceutically acceptable salt, a solvate or a hydrate thereof according to the present invention, or in any of the above applicable embodiments, $R_3$ is absent or represents 1 or 2 identical or different substituents present on the phenyl ring, each $R_3$ is independently selected from the group consisting of: hydrogen, halogen, hydroxyl, $C_{1-4}$alkoxy (e.g. methoxy), carboxyl, diethylamino, phenyl and acetylamino, and, when the phenyl ring is monosubstituted with $R_3$ at position 4, $R_3$ is not a bromine atom.

In another preferred embodiment of the present invention, in the compound of Formula Ib, or a racemate or an optical isomer thereof, or a pharmaceutically acceptable salt, a solvate or a hydrate thereof according to the present invention, or in any of the above applicable embodiments, $R_3$ is absent or represents 2 identical or different substituents present on the phenyl ring, the phenyl ring is monosubstituted with $R_3$ at position 3 or 4, and $R_3$ is selected from the group consisting of: hydrogen, chlorine, hydroxyl, $C_{1-4}$alkoxy (e.g. methoxy), carboxyl, diethylamino, phenyl and acetylamino.

In another preferred embodiment of the present invention, in the compound of Formula Ib, or a racemate or an optical isomer thereof, or a pharmaceutically acceptable salt, a solvate or a hydrate thereof according to the present invention, or in any of the above applicable embodiments, $R_3$ is absent or represents 2 identical or different substituents present on the phenyl ring, the phenyl ring is disubstituted with $R_3$ at positions 2 and 4, and each $R_3$ is independently selected from the group consisting of: hydrogen, chlorine, fluorine, bromine, hydroxyl, $C_{1-4}$alkoxy (e.g. methoxy), carboxyl, diethylamino, phenyl and acetylamino.

In another preferred embodiment of the present invention, in the compound of Formula Ib, or a racemate or an optical isomer thereof, or a pharmaceutically acceptable salt, a solvate or a hydrate thereof according to the present invention, or in any of the above applicable embodiments, $R_3$ is absent or represents 2 identical or different substituents present on the phenyl ring, the phenyl ring is disubstituted with $R_3$ at positions 4 and 5, each $R_3$ is independently selected from the group consisting of: hydrogen, chlorine, fluorine, bromine, hydroxyl, $C_{1-4}$alkoxy (e.g. methoxy), carboxyl, diethylamino, phenyl and acetylamino.

In another preferred embodiment of the present invention, in the compound of Formula Ib, or a racemate or an optical isomer thereof, or a pharmaceutically acceptable salt, a solvate or a hydrate thereof according to the present invention, or in any of the above applicable embodiments, $R_3$ is absent or represents 2 identical or different substituents present on the phenyl ring, the phenyl ring is disubstituted with $R_3$ at positions 2 and 6, and each $R_3$ is independently selected from the group consisting of: hydrogen, chlorine, fluorine, bromine, hydroxyl, $C_{1-4}$alkoxy (e.g. methoxy), carboxyl, diethylamino, phenyl and acetylamino.

In another preferred embodiment of the invention, in the compound of Formula Ic, or a racemate or an optical isomer thereof, or a pharmaceutically acceptable salt, a solvate or a hydrate thereof according to the present invention, or in any of the above applicable embodiments, $R_3$ is absent or represents 1, 2, 3 or 4 identical or different substituents present on the phenyl ring, each $R_3$ is independently selected from the group consisting of: hydrogen, halogen, hydroxyl, $C_{1-4}$alkyl, $C_{1-4}$haloalkyl, $C_{1-4}$alkoxy, amino, amino monosubstituted or disubstituted with $C_{1-4}$alkyl, carboxyl, R'(C=O)NH— and phenyl, wherein R' is $C_{1-4}$alkyl.

In another preferred embodiment of the present invention, in the compound of Formula Ic, or a racemate or an optical isomer thereof, or a pharmaceutically acceptable salt, a solvate or a hydrate thereof according to the present invention, or in any of the above applicable embodiments, $R_3$ is absent or represents 1 or 2 identical or different substituents present on the phenyl ring, $R_3$ is selected from the group consisting of: hydrogen, chlorine, fluorine, bromine, hydroxyl, $C_{1-4}$alkoxy (e.g. methoxy), carboxyl, diethylamino, phenyl and acetylamino.

In another preferred embodiment of the present invention, in the compound of Formula Id, or a racemate or an optical isomer thereof, or a pharmaceutically acceptable salt, a solvate or a hydrate thereof according to the present invention, or in any of the above applicable embodiments, $R_3$ is absent or represents 1, 2, or 3 identical or different substituents present on the phenyl ring, and each $R_3$ is independently selected from the group consisting of: hydrogen, halogen, hydroxyl, $C_{1-6}$alkyl, $C_{1-6}$haloalkyl, $C_{1-6}$alkoxy, amino, amino monosubstituted or disubstituted with $C_{1-6}$alkyl, carboxyl, R'(C=O)NH— and phenyl, wherein R' is $C_{1-6}$alkyl.

In another preferred embodiment of the present invention, in the compound of Formula Id, or a racemate or an optical isomer thereof, or a pharmaceutically acceptable salt, a solvate or a hydrate thereof according to the present invention, or in any of the above applicable embodiments, $R_3$ is absent or represents 1, 2, or 3 identical or different substituents present on the phenyl ring, each $R_3$ is independently selected from the group consisting of: hydrogen, halogen, hydroxyl, $C_{1-4}$alkyl, $C_{1-4}$haloalkyl, $C_{1-4}$alkoxy, amino, amino monosubstituted or disubstituted with $C_{1-4}$alkyl, carboxyl, R'(C=O)NH— and phenyl, wherein R' is $C_{1-4}$alkyl.

In another preferred embodiment of the present invention, in the compound of Formula Id, or a racemate or an optical isomer thereof, or a pharmaceutically acceptable salt, a solvate or a hydrate thereof according to the present invention, or in any of the above applicable embodiments, $R_3$ on one phenyl ring is hydrogen, the other phenyl ring is substituted with one $R_3$ selected from fluorine, chlorine, bromine, hydroxyl, carboxyl, amino, methyl, ethyl, propyl, methoxy, ethoxy, propoxy, dimethylamino, diethylamino, and acetylamino.

In another preferred embodiment of the present invention, in the compound of Formula Id, or a racemate or an optical isomer thereof, or a pharmaceutically acceptable salt, a solvate or a hydrate thereof according to the present invention, or in any of the above applicable embodiments, $R_3$ on one phenyl ring is hydrogen, the other phenyl ring is substituted at position 4 with one $R_3$ selected from fluorine, chlorine, bromine, hydroxyl, carboxyl, amino, methyl, ethyl, propyl, methoxy, ethoxy, propoxy, dimethylamino, diethylamino and acetylamino.

In the invention, the substitution position of $R_3$ on the phenyl ring is as follows:

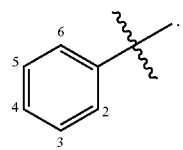

In a preferred embodiment of the present invention, the compound of Formula I, a racemate or an optical isomer thereof, or a pharmaceutically acceptable salt, a solvate or a hydrate thereof, is selected from the group consisting of:

Naphthalene-1-sulfonic acid [5-(2,4-dichloro-benzylidene)-4-oxo-4,5-dihydro-thiazol-2-yl] amide (Compound 1), Naphthalene-1-sulfonic acid [5-(3-methoxy-4-hydroxy-benzylidene)-4-oxo-4,5-dihydro-thiazol-2-yl] amide (Compound 2), Naphthalene-1-sulfonic acid [5-(2-hydroxy-4-diethylamino-benzylidene)-4-oxo-4,5-dihydro-thiazol-2-yl] amide (Compound 3), Naphthalene-1-sulfonic acid [5-(4-chloro-benzylidene)-4-oxo-4,5-dihydro-thiazol-2-yl] amide (Compound 4), Naphthalene-1-sulfonic acid [5-(4-carboxy-benzylidene)-4-oxo-4,5-dihydro-thiazol-2-yl] amide (Compound 5), Naphthalene-1-sulfonic acid [5-(3-hydroxy-benzylidene)-4-oxo-4,5-dihydro-thiazol-2-yl] amide (Compound 6), Naphthalene-1-sulfonic acid [5-(3-hydroxy-4-methoxy-benzylidene)-4-oxo-4,5-dihydro-thiazol-2-yl] amide (Compound 7), Naphthalene-1-sulfonic acid [5-(3-bromo-4-hydroxy-benzylidene)-4-oxo-4,5-dihydro-thiazol-2-yl] amide (Compound 8), Naphthalene-1-sulfonic acid [5-(2,6-dimethoxy-benzylidene)-4-oxo-4,5-dihydro-thiazol-2-yl] amide (Compound 9), Naphthalene-1-sulfonic acid [5-(2-chloro-4-fluoro-benzylidene)-4-oxo-4,5-dihydro-thiazol-2-yl] amide (Compound 10), Naphthalene-1-sulfonic acid (5-biphenyl-4-yl-methylene-4-oxo-4,5-dihydro-thiazol-2-yl) amide (Compound 11), Naphthalene-1-sulfonic acid [5-(4-acetylamino-benzylidene)-4-oxo-4,5-dihydro-thiazol-2-yl] amide (Compound 12), Naphthalene-1-sulfonic acid (4-oxo-5-phenylamino-4,5-dihydro-thiazol-2-yl) amide (Compound 13), and Naphthalene-1-sulfonic acid {5-[(4-bromo-phenyl)-phenyl-methyl]-4-oxo-4,5-dihydro-thiazol-2-yl} amide (Compound 14).

The compound represented by Formula I according to the first aspect of the present invention can be prepared by conventional synthetic routes as needed.

In a preferred embodiment of the present invention, the compound of Formula Ib, a racemate or an optical isomer thereof, or a pharmaceutically acceptable salt, a solvate or a hydrate thereof can be prepared exemplarily by the following reaction scheme:

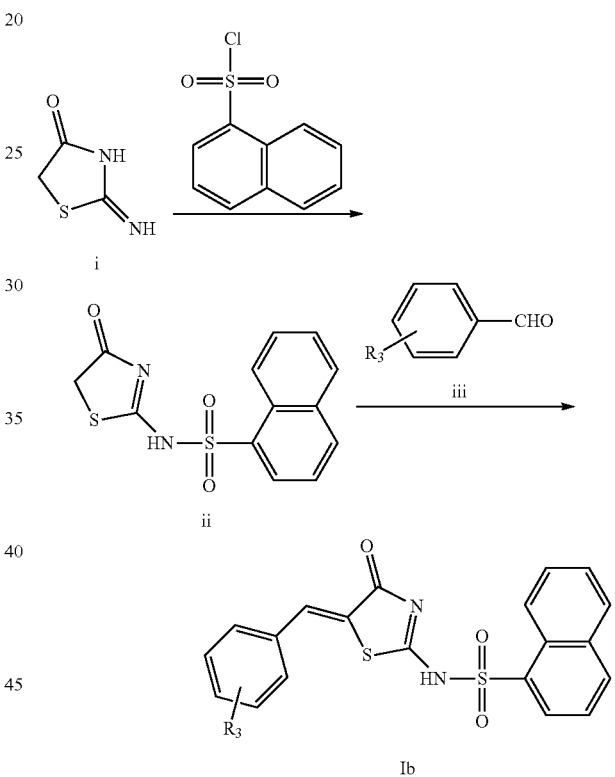

For example, 2-imino-4(5H)-thiazolinone represented by Formula i is used as a starting material, reacts with 1-naphthalenesulfonyl chloride by condensation reaction to produce a compound of Formula ii in tetrahydrofuran to which trimethylamine is added. in an ethanol solution containing piperidine as a catalyst, a compound of Formula Ib is produced by the condensation of the compound of Formula ii and a compound of Formula iii. The compound of Formula iii is benzaldehyde optionally monosubstituted or polysubstituted with $R_3$, wherein $R_3$ has the same meanings as defined in the first aspect of the present invention.

In a preferred embodiment of the present invention, the compound of Formula Ic, a racemate or an optical isomer thereof, or a pharmaceutically acceptable salt, a solvate or a hydrate thereof can be prepared exemplarily by the following reaction scheme:

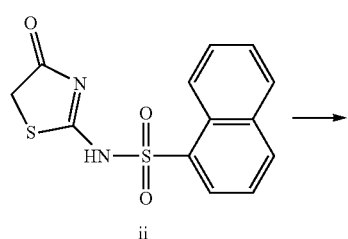

ii

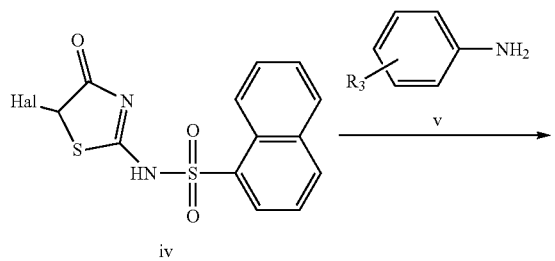

iv

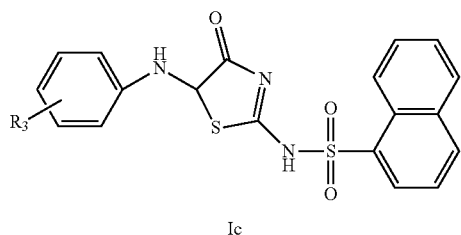

Ic

For example, a compound of Formula ii is used as a raw material. In a mixed solution containing chloroform and ethyl acetate, the compound of Formula ii is reacted with the added copper halide (preferably copper bromide) to produce a compound of Formula iv. In a DMF solution of potassium carbonate, the compound of Formula iv is reacted with phenylamine represented by Formula v to produce a compound of Formula Ic. The compound of Formula v is phenylamine optionally monosubstituted or polysubstituted with $R_3$, wherein $R_3$ has the same meanings as defined in the first aspect of the present invention. In Formula iv, Hal is halogen (preferably Br).

In a preferred embodiment of the present invention, the compound of Formula Id, a racemate or an optical isomer thereof, or a pharmaceutically acceptable salt, a solvate or a hydrate thereof can be prepared exemplarily by the following reaction scheme:

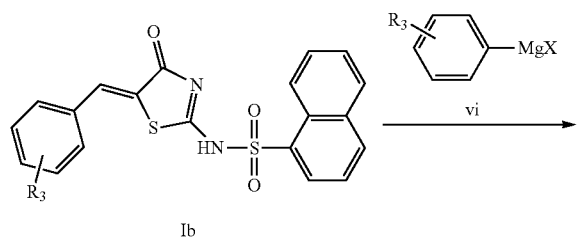

Ib

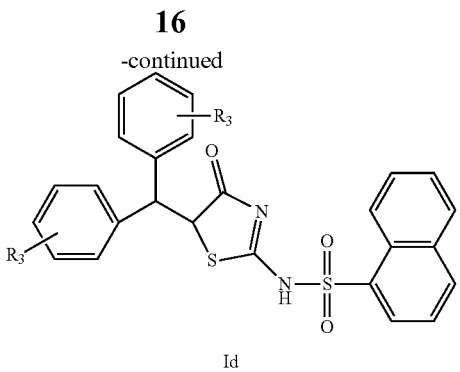

Id

For example, the compound of Formula Ib can be used as a raw material. The compound of Formula Ib is added into anhydrous tetrahydrofuran, a catalytic amount of cuprous chloride is added, and at −20° C., a compound of Formula vi is added dropwise to produce a compound of Formula Id, wherein $R_3$ has the same meanings as defined in the first aspect of the present invention, and in Formula vi, X is halogen (preferably Br).

In the second aspect, the invention relates to a pharmaceutical composition, comprising at least the compound represented by Formula I, Formula Ia, Formula Ib, Formula Ic or Formula Id, a racemate or an optical isomer thereof, or a pharmaceutically acceptable salt, a solvate or a hydrate thereof according to the first aspect of the present invention, and one or more pharmaceutically acceptable carriers or excipients.

In the third aspect, the invention relates to use of the compound represented by Formula I, Formula Ia, Formula Ib, Formula Ic or Formula Id, a racemate or an optical isomer thereof or a pharmaceutically acceptable salt, a solvate or a hydrate thereof according to the first aspect of the present invention or the pharmaceutical composition according to the second aspect of the present invention in the manufacture of a medicament for treating and/or preventing a disease or disorder associated with a viral infection. Said viral infection includes, but is not limited to: an infection caused by a virus such as rhinovirus, enterovirus (e.g. EV71), cardiovirus, hepacivirus, influenza virus, SARS virus, Ebola virus, hemorrhagic fever virus, and human immunodeficiency virus. Said disease or disorder associated with a viral infection is selected from the group consisting of respiratory disease (including but not limited to: common cold (e.g. summer cold), pharyngitis, tonsillitis and croup), digestive system disease, hemorrhagic fever disease, meningitis/encephalitis, immunodeficiency disease, hepatitis, hand-foot-mouth disease, nervous system disease (including aseptic meningitis, encephalitis and polio-like paralysis), and neurogenic pulmonary edema, etc.

In the fourth aspect, the present invention relates to the compound of Formula I, Formula Ia, Formula Ib, Formula Ic or Formula Id, a racemate or an optical isomer thereof, or a pharmaceutically acceptable salt, a solvate or a hydrate thereof according to the first aspect of the present invention, or the pharmaceutical composition according to the second aspect of the present invention, for use in the treatment and/or prevention of a disease or disorder associated with a viral infection. Said viral infection includes, but is not limited to: an infection caused by a virus such as rhinovirus, enterovirus (e.g. EV71), cardiovirus, hepacivirus, influenza virus, SARS virus, Ebola virus, hemorrhagic fever virus, and human immunodeficiency virus. Said disease or disorder associated with a viral infection is selected from the group consisting of respiratory disease (including but not limited to: common cold (e.g. summer cold), pharyngitis, tonsillitis and croup), digestive system disease, hemorrhagic fever disease, meningitis/encephalitis, immunodeficiency disease, hepatitis, hand-foot-mouth disease, nervous system disease (including aseptic meningitis, encephalitis and polio-like paralysis), and neurogenic pulmonary edema, etc.

In the fifth aspect, the present invention relates to a method for treatment and/or prevention a disease or disorder associated with a viral infection, comprising administering to a subject in need thereof a therapeutically or prophylactically effective amount of at least one of the compound represented by Formula I, Formula Ia, Formula Ib, Formula Ic or Formula Id, a racemate or an optical isomer thereof, or a pharmaceutically acceptable salt, a solvate or a hydrate thereof according to the first aspect of the present invention. Said viral infection includes, but is not limited to: an infection caused by a virus such as rhinovirus, enterovirus (e.g. EV71), cardiovirus, hepacivirus, influenza virus, SARS virus, Ebola virus, hemorrhagic fever virus, and human immunodeficiency virus. Said disease or condition associated with a viral infection is selected from the group consisting of respiratory disease (including but not limited to: common cold (e.g. summer cold), pharyngitis, tonsillitis and croup), digestive system disease, hemorrhagic fever disease, meningitis/encephalitis, immunodeficiency disease, hepatitis, hand-foot-mouth disease, nervous system disease (including aseptic meningitis, encephalitis and polio-like paralysis), and neurogenic pulmonary edema, etc.

The features included in any aspect of the invention or any sub-aspect of the aspect are also applicable to any other aspect of the present invention or any sub-aspect of the other aspect. In the present invention, for example, when "the first aspect of the invention" is mentioned, the "any sub-aspect" refers to any sub-aspect of the first aspect of the present invention, and when another aspect is mentioned in a similar manner, it also has the same meanings.

The aspects and characteristics of the present invention are further described as follows.

The terms and phrases used in the present invention have the general meanings well known by a person skilled in the art, nevertheless, the present invention still intends to describe and explain these terms and phrases again in detail. If the meanings of the terms and phrases mentioned herein are inconsistent with the well-known meanings, the meanings expressed in the present invention will prevail.

As used herein, the term "pharmaceutically acceptable", for example, in the expression "pharmaceutically acceptable salt", means that the salt is not only physiologically acceptable in a subject, but also refers to a synthetic substance having an application value in pharmacology.

The term "alkyl" as used herein refers to a saturated linear or branched monovalent hydrocarbon group, preferably having 1-12 carbon atoms, further preferably having 1-10, 1-8, 1-6, 1-4 or 1-3 carbon atoms. The term "$C_{1-8}$alkyl" refers to an alkyl having a specified number of carbon atoms, which is a linear or branched alkyl, and may include its subgroup, such as $C_{1-6}$alkyl, $C_{1-4}$alkyl, $C_{1-3}$ alkyl, $C_{1-2}$alkyl, $C_{2-5}$alkyl, and $C_{2-4}$alkyl. Typical examples of "alkyl" include, but are not limited to methyl, ethyl, n-propyl, isopropyl, n-butyl, isobutyl, sec-butyl, tert-butyl, n-pentyl, tert-pentyl, neopentyl, hexyl, heptyl, octyl, etc.

As used herein, the terms "halogen", "halogen atom", "halo-", and the like, represent fluorine, chlorine, bromine or iodine, particularly represent fluorine, chlorine, or bromine.

The term "amino" as used herein refers to —$NH_2$.
The term "hydroxyl" as used herein refers to —OH.
The term "carboxyl" as used herein refers to —C(O)OH.

The term "haloalkyl" as used herein refers to alkyl monosubstituted or polysubstituted with halogen such as fluorine, chlorine, bromine or iodine. The preferred haloalkyl is chloromethyl, chloroethyl, dichloroethyl, trifluoromethyl, difluoromethyl, monofluoromethyl, etc.

The term "alkoxy" as used herein refers to the group —OR", wherein R" refers to an alkyl having the same meanings as defined above. Typical examples of "alkoxy" include, but are not limited to methoxy, ethoxy, n-propoxy, isopropoxy, n-butoxy, isobutoxy, tert-butoxy, sec-butoxy, n-pentoxy, n-hexoxy, 1,2-dimethylbutoxy, etc.

The groups as defined by the terms above can also be optionally monosubstiuted or polysubstituted with —CN, —OH, —$NH_2$, $C_{1-4}$alkyl, $C_{1-4}$alkoxy or halogen.

The term "acylamino" as used herein refers to the group R'(C=O)NH—, wherein R' refers to an alkyl having the same meanings as defined above, preferably $C_{1-8}$ alkyl. Typical examples of "acylamino" include, but are not limited to formamido, acetylamino.

If the name of a compound used herein is not consistent with its chemical formula, the chemical formula shall prevail.

The term "an effective amount" as used herein refers to an amount that can achieve the treatment and/or prevention of said disease or condition according to the present invention in a subject.

The term "pharmaceutical composition" as used herein, which may also refer to "composition", can be used in the treatment and/or prevention of said disease or disorder according to the present invention in a subject, particularly in a mammal.

The term "subject" as used herein may refers to a patient or an animal to whom the compound of Formula I or a pharmaceutical composition thereof according to the present invention is administered in order to treat and/or prevent said disease or disorder according to the present invention, particularly a mammal, such as human, dog, monkey, cow, and horse.

As used herein, if not specifically indicated, "%" refers to a weight-to-weight percentage, particularly when describing a solid substance. Of course, when describing a liquid substance, the "%" may refers to a weight-to-volume percentage (under the circumstance where a solid is dissolved in a liquid), or a volume-to-volume percentage (under the circumstance where a liquid is dissolved in a liquid).

In the present invention, said viral infection includes, but is not limited to: an infection caused by a virus such as rhinovirus, enterovirus, cardiovirus, hepacivirus, influenza virus, SARS virus, Ebola virus, hemorrhagic fever virus, and human immunodeficiency virus (AIDS virus), preferably an infection caused by an enterovirus, for example, an infection caused by an EV71.

In the present invention, said disease or disorder associated with a viral infection is selected from the group consisting of respiratory disease (including but not limited to: common cold (e.g. summer cold), pharyngitis, tonsillitis and croup), digestive system disease, hemorrhagic fever disease, meningitis/encephalitis, immunodeficiency disease, hepatitis, hand-foot-mouth disease, nervous system disease (including aseptic meningitis, encephalitis and polio-like paralysis), and neurogenic pulmonary edema, etc., wherein the disease or disorder associated with an EV71 infection includes hand-foot-mouth disease, nervous system disease (including aseptic meningitis, encephalitis and polio-like paralysis), and neurogenic pulmonary edema, etc.

In an embodiment of the present invention, it relates to a method for prevention and/or treatment of a disease associated with an infection by a virus including rhinovirus, enterovirus, cardiovirus, human immunodeficiency virus, hepacivirus, influenza virus, SARS virus, Ebola virus, hemorrhagic fever virus, etc., comprising administering a therapeutically or prophylactically effective amount of at least one of the compound of Formula I or a pharmaceutically acceptable salt thereof or a hydrate thereof to a patient in need of preventing and/or treating a disease associated with an infection by a virus including rhinovirus, enterovirus, cardiovirus, human immunodeficiency virus, hepacivirus, influenza virus, SARS virus, Ebola virus, hemorrhagic fever virus, etc.

The compounds according to the present invention are a class of novel broad-spectrum antiviral inhibitors, and are particularly characterized by the capability of treating a disease caused by a virus such as rhinovirus, enterovirus, human immunodeficiency virus, hepacivirus, influenza virus, SARS virus, Ebola virus, or hemorrhagic fever virus. Said disease caused by the virus includes, but is not limited to: respiratory disease, digestive system disease, hemorrhagic fever disease, meningitis/encephalitis, immunodeficiency disease, hepatitis, hand-foot-mouth disease, nervous system disease (including aseptic meningitis, encephalitis and polio-like paralysis), neurogenic pulmonary edema, etc.

The respiratory disease includes, but is not limited to: common cold (summer cold), pharyngitis, tonsillitis, and croup.

According to the present invention, the pharmaceutical composition of the compound according to the invention may be administered by any of the following means: oral administration, spray inhalation, rectal administration, intranasal administration, buccal administration, vaginal administration, topical administration, parenteral administration such as subcutaneous, intravenous, intramuscular, intraperitoneal, intrathecal, intraventricular, intrasternal and intracranial injection or input, or administration by virtue of an explant reservoir. Among them, oral administration, intraperitoneal administration, or intraventricular administration is preferred. In addition, in order to effectively treat central nervous system disorders with the compound according to the present invention, intraventricular administration is preferred to overcome the possible low blood-brain barrier permeability of the compound.

When orally administered, the compound according to the present invention may be prepared in the form of any orally acceptable formulation, including, but not limited to a tablet, a capsule, an aqueous solution, or an aqueous suspension. The carriers for use in a tablet generally include lactose and maize starch. In addition, a lubricant such as magnesium stearate can also be added. Diluents for use in a capsule generally include lactose and dry maize starch. An aqueous suspension is generally obtained by mixing an active ingredient with a suitable emulsifying agent and a suitable suspending agent. If necessary, a sweetening agent, a flavoring agent or a coloring agent may be added to the above-mentioned forms of oral formulations.

When rectally administrated, the compound according to the present invention is generally prepared in a form of a suppository, by mixing a drug with a suitable nonirritant excipient. The excipient is present in a form of solid at room temperature, and is melt to release the drug at rectal temperature. Such excipients include cacao butter, beeswax and polyethylene glycol.

When topically administrated, particularly when treating a neurogenic disease at the affected part or organ that is easily accessible by topical application, such as eyes, skin or lower intestine, the compound according to the present invention may be prepared in different forms of formulations for topical application depending on the affected part or organ. Specific illustration is as follows.

When topically administrated to eyes, the compound according to the present invention may be prepared in a form of a micronized suspension or a solution, and a carrier used is a sterile saline that is isotonic and is at a certain pH, wherein a preservative such as chloride benzyl alkoxide may be added or not. In addition, for ophthalmic use, the compound may also be prepared in a form of ointment such as vaseline ointment.

When topically administrated to skin, the compound according to the present invention may be prepared in a suitable form of an ointment, a lotion or a cream, wherein the active ingredient is suspended or dissolved in one or more carriers. The carriers for use in an ointment preparation include, but are not limited to: mineral oil, liquid paraffin, white vaseline, propylene glycol, polyethylene oxide, polypropylene oxide, emulsion wax and water; carriers for use in a lotion and a cream include, but are not limited to: mineral oil, sorbitan monostearate, Tween 60, hexadecylester wax, hexadecane aromatic alcohol, 2-octyl dodecanol, benzyl alcohol and water.

When topically administrated to lower intestine, the compound according to the present invention may be prepared in a form of the rectal suppository as described above or a suitable enema formulation, and may also be prepared in a form of a topical transdermal patch.

The compound according to the present invention may be administered in a form of a sterile formulation for injection, including a sterile injection water, an oil suspension or a sterile injection solution. The carriers and solvents for use therein include water, Ringer's solution, and isotonic sodium chloride solution. In addition, a sterile fixed oil can also be used as a solvent or a suspension medium, such as monoglyceride or diglyceride.

As used herein, the term "a therapeutically effective amount" refers to an amount within a reasonable range of medical judgment, which is sufficient to treat or prevent a disease but is sufficiently low to avoid severe side effects in a patient (at a reasonable benefit-risk ratio). The therapeutically effective amount of a compound depends on factors such as the compound selected (for example, taken into account the efficacy, effectiveness and half-life of the compound), the administration route selected, the disease to be treated, the severity of the disease to be treated, the age, size, body weight, and physical diseases of the patient to be treated, the medical history of the patient to be treated, the period of time for treatment, the properties of the additional therapy used simultaneously, and the desired therapeutic effect, but still can be determined by a person skilled in the art.

In addition, it has to be pointed out that the specific dose of the compound according to the present invention and the method of using the compound according to the present invention depend on a lot of factors for a different patient, including age, body weight, gender, natural health condition, and nutritional state of a patient, activity of a compound, administration time, metabolic rate, severity of a disease, and subjective judgment made by a Physician. The preferred dose here is between 0.01 and 100 mg/kg body weight/day.

SPECIFIC MODES FOR CARRYING OUT THE INVENTION

The invention can be further illustrated by the following examples and experimental examples. However, the scope of the invention is not limited to the following examples and experimental examples. A person skilled in the art can understand that without departing from the spirit and scope of the invention, various changes and modifications can be made to the present invention. The materials and experimental methods used in the experiments are generally and/or specifically described in the present invention. Although many materials and operational methods used for achieving the purpose of the present invention are well known in the art, the present invention still describes them in detail as much as possible.

In all the following examples, standard operations and purification methods known by a person skilled in the art can be employed. Unless otherwise specified, all the temperatures are expressed as ° C. (Celsius degrees). The structure of a compound is identified by Nuclear Magnetic Resonance (NMR) or mass spectrometry (MS). The melting point (m.p.) of a compound is determined by RY-1 Type melting-point apparatus, the thermometer is not calibrated, and m.p. is expressed as ° C. $^1$H NMR is determined by JNM-ECA-400 Type NMR spectrometer (JEOL Ltd.). Mass spectrum is determined by API3000 (ESI) Type mass spectrometer. If not indicated, all the solvents for use in reaction have been subjected to standardized pretreatment.

Example 1 Synthesis of Naphthalene-1-sulfonic acid [5-(2,4-dichloro-benzylidene)-4-oxo-4,5-dihydro-thiazol-2-yl] amide (Compound 1)

1.1 Synthesis of Naphthalene-1-sulfonic acid (4-oxo-4,5-dihydro-thiazol-2-yl) amide Naphthalene-1-sulfonyl chloride (30.95 g, 0.14 mol), 2-imino-4(5H)-thiazolinone (16.00 g, 0.14 mol) and triethylamine (40 ml) were added into tetrahydrofuran (800 ml). The resultant mixture was heated to reflux, and reacted overnight. The reaction solution was cooled, and ethyl acetate (1500 ml) was added. The resultant mixture was washed with water for three times, to obtain an organic phase. The organic phase was dried with anhydrous sodium sulphate, filtrated, and concentrated. The residue was purified by silica gel column chromatography, to obtain a yellow brown solid, which was dried and weighed as 10.70 g, with a yield of 25%. 1H-NMR (400 MHz, DMSO-d6) δ: 12.54 (s, 1H), 8.60 (d, 1H), 8.29-8.23 (dd, 2H), 8.10 (d, 1H), 7.71-7.67 (m, 3H), 4.04 (s, 2H). ESI-MS (m/z): 307.3 [M+H]+.

1.2 Synthesis of Naphthalene-1-sulfonic acid [5-(2, 4-dichloro-benzylidene)-4-oxo-4,5-dihydro-thiazol-2-yl] amide (Compound 1)

The compound Naphthalene-1-sulfonic acid (4-oxo-4,5-dihydro-thiazol-2-yl) amide (0.31 g, 1.0 mmol), 2,4-dichloro-benzaldehyde (0.21 g, 1.2 mmol) and ethanol (20 ml) were added to a reaction bottle, and 2 drops of piperidine were added under stirring. After reflux reaction for 8 h, the resultant mixture was cooled and filtrated. The filter cake was washed with acetone, and diethyl ether, to obtain a yellow solid (0.27 g), with a yield of 63.0%. 1H-NMR (400 MHz, DMSO-d6) δ: 8.59 (d, 1H), 8.30 (d, 1H), 8.28 (d, 1H), 8.12 (d, 1H), 7.89 (s, 1H), 7.79-7.68 (m, 6H), 7.34 (s, 1H). ESI-MS (m/z): 461.0 [M−H]−.

Example 2 Synthesis of Naphthalene-1-sulfonic acid [5-(3-methoxy-4-hydroxy-benzylidene)-4-oxo-4,5-dihydro-thiazol-2-yl] amide (Compound 2)

By the method as described in Item 1.2 of Example 1, 2,4-dichloro-benzaldehyde in the reactants was replaced with 3-methoxy-4-hydroxy-benzaldehyde, to obtain a yellow solid (0.25 g), with a yield of 56.8%. 1H-NMR (400 MHz, DMSO-d6) δ: 10.13 (s, 1H), 8.60 (d, 1H), 8.30 (dd, 2H), 8.12 (d, 1H), 7.73-7.69 (m, 4H), 7.27 (m, 1H), 7.18 (m, 1H), 7.00 (m, 1H), 4.04 (s, 3H). ESI-MS (m/z): 439.0 [M−H]−.

Example 3 Synthesis of Naphthalene-1-sulfonic acid [5-(2-hydroxy-4-diethylamino-benzylidene)-4-oxo-4,5-dihydro-thiazol-2-yl] amide (Compound 3)

By the method as described in Item 1.2 of Example 1, 2,4-dichloro-benzaldehyde in the reactants was replaced with 2-hydroxy-4-diethylamino-benzaldehyde, to obtain a red solid (0.25 g), with a yield of 51.9%. 1H-NMR (400 MHz, DMSO-d6) δ: 12.76 (s, 1H), 10.42 (s, 1H), 8.60 (d, 1H), 8.30 (dd, 2H), 8.11 (d, 1H), 7.91 (s, 1H), 7.70 (m, 3H), 7.26 (d, 1H), 6.49 (m, 1H), 6.20 (s, 1H), 3.38 (q, 4H), 1.14 (t, 6H). ESI-MS (m/z): 480.1 [M−H]−.

Example 4 Synthesis of Naphthalene-1-sulfonic acid [5-(4-chloro-benzylidene)-4-oxo-4,5-dihydro-thiazol-2-yl] amide (Compound 4)

By the synthetic method as described in Item 1.2 of Example 1, 2,4-dichloro-benzaldehyde in the reactants was replaced with 4-chloro-benzaldehyde, to obtain a yellow solid (0.27 g), with a yield of 62.9%. 1H-NMR (400 MHz, DMSO-d6) δ: 8.70 (d, 1H), 8.18 (d, 1H), 8.12 (d, 1H), 8.00 (d, 1H), 7.63-7.55 (m, 8H), 7.34 (s, 1H). ESI-MS (m/z): 427.0 [M−H]−.

Example 5 Synthesis of Naphthalene-1-sulfonic acid [5-(4-carboxy-benzylidene)-4-oxo-4,5-dihydro-thiazol-2-yl] amide (Compound 5)

By the synthetic method as described in Item 1.2 of Example 1, 2,4-dichloro-benzaldehyde in the reactants was replaced with 4-carboxy-benzaldehyde, to obtain a yellow solid (0.25 g), with a yield of 57.1%. 1H-NMR (400 MHz, DMSO-d6) δ: 8.60 (d, 1H), 8.30 (d, 2H), 8.12 (m, 2H), 8.10 (s, 1H), 7.81-7.67 (m, 6H). ESI-MS (m/z): 437.0 [M−H]−.

Example 6 Synthesis of Naphthalene-1-sulfonic acid [5-(3-hydroxy-benzylidene)-4-oxo-4,5-dihydro-thiazol-2-yl] amide (Compound 6)

By the synthetic method as described in Item 1.2 of Example 1, 2,4-dichloro-benzaldehyde in the reactants was replaced with 3-hydroxy-benzaldehyde, to obtain a yellow solid (0.24 g), with a yield of 58.5%. 1H-NMR (400 MHz, DMSO-d6) δ: 10.01 (s, 1H), 8.60 (d, 1H), 8.31 (dd, 2H), 8.12 (d, 1H), 7.78-7.67 (m, 4H), 7.37 (m, 1H), 7.12 (m, 2H), 6.93 (m, 1H). ESI-MS (m/z): 409.0 [M−H]−.

Example 7 Synthesis of Naphthalene-1-sulfonic acid [5-(3-hydroxy-4-methoxy-benzylidene)-4-oxo-4,5-dihydro-thiazol-2-yl] amide (Compound 7)

By the synthetic method as described in Item 1.2 of Example 1, 2,4-dichloro-benzaldehyde in the reactants was replaced with 3-hydroxy-4-methoxy-benzaldehyde, to obtain a yellow solid (0.25 g), with a yield of 56.8%. 1H-NMR (400 MHz, DMSO-d6) δ: 13.06 (brs, 1H), 9.73 (s, 1H), 8.59 (d, 1H), 8.30 (d, 2H), 8.12 (d, 1H), 7.77-7.69 (m, 3H), 7.63 (s, 1H), 7.16-7.12 (m, 3H), 3.86 (s, 3H). ESI-MS (m/z): 439.0 [M−H]−.

Example 8 Synthesis of Naphthalene-1-sulfonic acid [5-(3-bromo-4-hydroxy-benzylidene)-4-oxo-4,5-dihydro-thiazol-2-yl] amide (Compound 8)

By the synthetic method as described in Item 1.2 of Example 1, 2,4-dichloro-benzaldehyde in the reactants was replaced with 3-bromo-4-hydroxy-benzaldehyde, to obtain a yellow solid (0.26 g), with a yield of 53.1%. 1H-NMR (400 MHz, DMSO-d6) δ: 11.05 (brs, 1H), 8.67 (d, 1H), 8.22 (m, 3H), 8.07 (d, 1H), 7.71-7.64 (m, 4H), 7.44 (m, 2H), 7.12 (d, 1H). ESI-MS (m/z): 488.9 [M–H]–.

Example 9 Synthesis of Naphthalene-1-sulfonic acid [5-(2,6-dimethoxy-benzylidene)-4-oxo-4,5-dihydro-thiazol-2-yl] amide (Compound 9)

By the synthetic method as described in Item 1.2 of Example 1, 2,4-dichloro-benzaldehyde in the reactants was replaced with 2,6-dimethoxy-benzaldehyde, to obtain a yellow solid (0.27 g), with a yield of 59.4%. 1H-NMR (400 MHz, DMSO-d6) δ: 8.60 (d, 1H), 8.30 (m, 2H), 8.12 (m, 2H), 7.77-7.68 (m, 3H), 7.30 (m, 1H), 6.78 (d, 1H), 6.74 (d, 1H), 3.87 (s, 3H), 3.75 (s, 3H). ESI-MS (m/z): 453.1 [M–H]–.

Example 10 Synthesis of Naphthalene-1-sulfonic acid [5-(2-chloro-4-fluoro-benzylidene)-4-oxo-4,5-dihydro-thiazol-2-yl] amide (Compound 10)

By the synthetic method as described in Item 1.2 of Example 1, 2,4-dichloro-benzaldehyde in the reactants was replaced with 2-chloro-4-fluoro-benzaldehyde, to obtain a yellow solid (0.25 g), with a yield of 56.0%. 1H-NMR (400 MHz, DMSO-d6) δ: 8.70 (d, 1H), 8.16 (m, 3H), 8.02 (d, 1H), 7.66-7.60 (m, 4H), 7.52 (m, 1H), 7.40 (m, 1H). ESI-MS (m/z): 445.0 [M–H]–.

Example 11 Synthesis of Naphthalene-1-sulfonic acid (5-biphenyl-4-yl-methylene-4-oxo-4,5-dihydro-thiazol-2-yl) amide (Compound 11)

By the synthetic method as described in Item 1.2 of Example 1, 2,4-dichloro-benzaldehyde in the reactants was replaced with biphenyl-4-carbaldehyde, to obtain a reddish yellow solid (0.28 g), with a yield of 60.2%. 1H-NMR (400 MHz, DMSO-d6) δ: 8.61 (d, H, J=8.1 Hz), 8.31 (m, 2H), 8.12 (d, 1H, J=8.1 Hz), 7.92 (d, 2H, J=8.4 Hz), 7.83 (s, 1H), 7.80-7.70 (m, 7H), 7.54-7.42 (m, 3H). ESI-MS (m/z): 469.1 [M–H]–.

Example 12 Synthesis of Naphthalene-1-sulfonic acid [5-(4-acetylamino-benzylidene)-4-oxo-4,5-dihydro-thiazol-2-yl] amide (Compound 12)

By the synthetic method as described in Item 1.2 of Example 1, 2,4-dichloro-benzaldehyde in the reactants was replaced with 4-acetylamino-benzaldehyde, to obtain a yellow solid (0.26 g), with a yield of 57.6%. 1H-NMR (400 MHz, DMSO-d6) δ: 10.28 (s, 1H), 8.64 (d, 1H, J=8.4 Hz), 8.27 (d, 1H, J=7.3 Hz), 8.22 (d, 1H, J=8.2 Hz), 7.77-7.53 (m, 8H), 2.90 (s, 3H, CH3). ESI-MS (m/z): 450.1 [M–H]–.

Example 13 Synthesis of Naphthalene-1-sulfonic acid (4-oxo-5-phenylamino-4,5-dihydro-thiazol-2-yl) amide (Compound 13)

13.1 Synthesis of Naphthalene-1-sulfonic acid (5-bromo-4-oxo-4,5-dihydro-thiazol-2-yl) amide The compound Naphthalene-1-sulfonic acid (5-bromo-4-oxo-4,5-dihydro-thiazol-2-yl) amide (6.10 g, 20.0 mmol) was added into a mixed solution of chloroform and ethyl acetate (volume ratio of 1:1) (300 ml), and heated to reflux, and copper bromide (9.5 g, 42.0 mmol) was added. The resultant mixture was reacted under reflux overnight. After the reaction was finished, the reaction solution was filtrated immediately, and the filtrate was concentrated. The residue was separated by silica gel column chromatography (eluant: dichloromethane/methanol (volume ratio of 9:1)), to obtain a white solid (2.15 g), with a yield of 28.1%. 1H-NMR (400 MHz, DMSO-d6) δ: 8.61 (d, 1H), 8.28 (dd, 2H), 8.12 (d, 1H), 7.73 (m, 3H), 5.95 (s, 1H); ESI-MS (m/z): 384.9 [M–H]–.

13.2 Synthesis of Naphthalene-1-sulfonic acid (4-oxo-5-phenylamino-4,5-dihydro-thiazol-2-yl) amide (Compound 13)

The compound Naphthalene-1-sulfonic acid (5-bromo-4-oxo-4,5-dihydro-thiazol-2-yl) amide (0.77 g, 2.0 mmol), phenylamine (0.19 g, 2.0 mmol) and potassium carbonate (0.55 g, 4.0 mmol) were added to DMF (15 ml). The resultant mixture was reacted at room temperature under stirring for 2 d, then water (30 ml) was added, and the mixture was extracted with dichloromethane (30 ml) for three times. The organic phases were combined, dried with anhydrous sodium sulphate, and filtered. The solvent was removed from the filtrate under reduced pressure, to obtain an oily substance. Ethyl acetate was added to the oily substance, and solid crude was precipitated under stirring, and then separated by silica gel column chromatography (eluant: dichloromethane/methanol (volume ratio of 8:1)), to obtain a yellow solid (0.15 g), with a yield of 18.9%. 1H-NMR (400 MHz, DMSO-d6) δ: 12.29 (brs, 1H), 8.56 (d, 1H), 8.27 (d, 1H), 8.23 (d, 1H), 8.10 (d, 1H), 7.70 (m, 3H), 7.18 (m, 2H), 7.00 (d, 1H), 6.79 (m, 1H), 6.53 (d, 2H), 6.38 (d, 1H); ESI-MS (m/z): 396.0 [M–H]–.

Example 14 Synthesis of Naphthalene-1-sulfonic acid {5-[(4-bromo-phenyl)-phenyl-methyl]-4-oxo-4,5-dihydro-thiazol-2-yl} amide (Compound 14)

The compound Naphthalene-1-sulfonic acid [5-(4-bromo-benzylidene)-4-oxo-4,5-dihydro-thiazol-2-yl] amide was added to tetrahydrofuran (15 ml), and a catalytic amount of copper chloride was added. At −20° C., 1.0 mol/L a solution of phenyl magnesium bromide in tetrahydrofuran (2 ml) was added dropwise, and the resultant mixture was reacted for 4 h after the addition. The reaction solution was heated to room temperature, and ice water was added to quench the reaction. The resultant mixture was extracted with dichloromethane, and the organic phase obtained was dried, filtrated, and concentrated. The residue was separated and purified by silica gel column chromatography, to obtain a yellow solid (0.15 g), with a yield of 13.6%. 1H-NMR (400 MHz, DMSO-d6) δ: 12.06 (brs, 1H), 8.48 (d, 1H), 8.31 (d, 1H), 8.18 (m, 2H), 7.70 (m, 3H), 7.48 (m, 1H), 7.31-7.13 (m, 7H), 7.20 (m, 1H), 5.56 (m, 1H), 4.83 (m, 1H). ESI-MS (m/z): 551.0 [M–H]–.

Examples 1-14 The chemical names and structural formulae of the prepared Compounds 1-14 and the positive control agent pitstop2 were shown in the following table.

| Compound No. | Name | Structural formula |
| --- | --- | --- |
| Con 1 (Pitstop 2) | Naphthalene-1-sulfonic acid [5-(4-bromo-benzylidene)-4-oxo-4,5-dihydro-thiazol-2-yl] amide | |
| 1 | Naphthalene-1-sulfonic acid [5-(2,4-dichloro-benzylidene)-4-oxo-4,5-dihydro-thiazol-2-yl] amide | |
| 2 | Naphthalene-1-sulfonic acid [5-(3-methoxy-4-hydroxy-benzylidene)-4-oxo-4,5-dihydro-thiazol-2-yl] amide | |
| 3 | Naphthalene-1-sulfonic acid [5-(2-hydroxy-4-diethylamino-benzylidene)-4-oxo-4,5-dihydro-thiazol-2-yl] amide | |
| 4 | Naphthalene-1-sulfonic acid [5-(4-chloro-benzylidene)-4-oxo-4,5-dihydro-thiazol-2-yl] amide | |
| 5 | Naphthalene-1-sulfonic acid [5-(4-carboxy-benzylidene)-4-oxo-4,5-dihydro-thiazol-2-yl] amide | |
| 6 | Naphthalene-1-sulfonic acid [5-(3-hydroxy-benzylidene)-4-oxo-4,5-dihydro-thiazol-2-yl] amide | |

-continued

| Compound No. | Name | Structural formula |
|---|---|---|
| 7 | Naphthalene-1-sulfonic acid [5-(3-hydroxy-4-methoxy-benzylidene)-4-oxo-4,5-dihydro-thiazol-2-yl] amide | |
| 8 | Naphthalene-1-sulfonic acid [5-(3-bromo-4-hydroxy-benzylidene)-4-oxo-4,5-dihydro-thiazol-2-yl] amide | |
| 9 | Naphthalene-1-sulfonic acid [5-(2,6-dimethoxy-benzylidene)-4-oxo-4,5-dihydro-thiazol-2-yl] amide | |
| 10 | Naphthalene-1-sulfonic acid [5-(2-chloro-4-fluoro-benzylidene)-4-oxo-4,5-dihydro-thiazol-2-yl] amide | |
| 11 | Naphthalene-1-sulfonic acid (5-biphenyl-4-yl-methylene-4-oxo-4,5-dihydro-thiazol-2-yl) amide | |
| 12 | Naphthalene-1-sulfonic acid [5-(4-acetylamino-benzylidene)-4-oxo-4,5-dihydro-thiazol-2-yl] amide | |
| 13 | Naphthalene-1-sulfonic acid (4-oxo-5-phenylamino-4,5-dihydro-thiazol-2-yl) amide | |

-continued

| Compound No. | Name | Structural formula |
|---|---|---|
| 14 | Naphthalene-1-sulfonic acid {5-[(4-bromo-phenyl)-phenyl-methyl]-4-oxo-4,5-dihydro-thiazol-2-yl} amide | |

Example 15 Antiviral Activity of the Compounds According to the Present Invention in an In Vitro Model 15.1 Test Items: Screening Compounds for Activity Against Enterovirus EV71

Test principle: Vero cell, MRC-5 cell, and RD cell were used as host of virus, respectively, and samples were tested for their inhibition of cytopathic effect (CPE) caused by virus.

1. Virus strain: enterovirus EV71 (SZ-98 strain, provided by Chinese Center for Disease Control and Prevention), Vero cell (provided by the Cell Bank of Chinese Academy of Sciences), MRC-5 cell (provided by the Cell Bank of Chinese Academy of Sciences), and RD cell (provided by the Cell Bank of Chinese Academy of Sciences), were subjected to passage culture, respectively, and stored at −80° C.

2. Sample treatment: a test sample (Compounds 1-14 and positive control agent) was dissolved in dimethyl sulfoxide (DMSO) to prepare a stock solution, which was stored at −20° C. The stock solution was diluted with DMEM medium (Gibco Company) containing 2% fetal bovine serum (Gibco Company) to prepare a 100 μM solution before use, and was 3-fold diluted with the medium to obtain 8 diluted concentrates.

3. Positive control agent: Con1 (pitstop2) (purchased from AmyJet Scientific Inc., Abcam), a broad-spectrum antiviral inhibitor.

4. Test method:

4.1 Therapeutic effect: the cells were seeded on a 96-well culture plate, and cultured in a 5% $CO_2$, 37° C. incubator for 24 h. About 100 TCID50 enterovirus EV71 was added to each well. After adsorption at 37° C. for 1 h, the virus solution was discarded, and a drug was added at different diluted concentrates, respectively. Meanwhile, virus control and cell control were set, and cultured at 37° C. When the cytopathic effect (CPE) of the virus control group reached 100% (all the cells exhibited pathological change), 100 μL Celltiter Glo detection reagent (Promega Corporation (US)) was added to each well, and the chemiluminescent value of each well was determined by Chemiluminescent Analyzer (Molecular Devices (US), Type: SpectraMax M5). The virus-inhibition rate of a sample at each concentration was calculated based on the chemiluminescent value, the sample concentration was used as abscissa, and the inhibition rate was used as ordinate, and S-Curve fitting was performed by using Origin software. Half maximal inhibitory concentration ($IC_{50}$) of each sample for enterovirus EV71 was calculated based on the fitting results. Median toxic concentration ($TC_{50}$) was determined by the same method. Selection index (SI) was determined by the ratio of $TC_{50}$ to $IC_{50}$, $SI=TC_{50}/IC_{50}$.

4.2 Preventive effect: the cells were seeded on a 96-well culture plate, and cultured in a 5% $CO_2$, 37° C. incubator for 24 h. To each well, a drug was added at a different diluted concentration, then the cells were cultured at 37° C. for 2 h, and then the drug was discarded. About 100 TCID50 enterovirus EV71 was added to each well, adsorbed at 37° C. for 1.5 h, then the virus solution was discarded, and a maintenance medium free of drug was added. Meanwhile, virus control and cell control were set, and cultured at 37° C. When the cytopathic effect (CPE) of the virus control group reached 100% (all the cells exhibited pathological change), the chemiluminescent value of each well was determined. The virus-inhibition rate of a sample at each concentration was calculated, and half maximal inhibitory concentration ($IC_{50}$), median toxic concentration ($TC_{50}$), and selection index (SI) of each sample for enterovirus EV71 were calculated. The methods for determining and calculating them were as described in Item 4.1

5. Test result

The activity-screening data of the positive control agent Con1 and Compounds 1-14 in the Examples was shown in the following table.

The activity-screening data on therapeutic effect was shown in Table 1-1 to Table 1-3, and the activity-screening data on preventive effect was shown in Table 2-1 to Table 2-2.

EV71 (SZ-98 strain) and Vero cell, RD cell were used as host of virus, and the results on activity of Compounds 1-14 against EV71 virus showed that the synthesized Compounds 3, 4, 5, 6, 8 and 14 had better anti-EV71 activity (having therapeutic effect on RD cell); among them, Compounds 3 and 4 had $IC_{50}$ of 7.41 μM and 5.75 μM, respectively, which were only second to the positive control compound Con 1 (5.14 μM), and the three compounds had the same cytotoxicity, all had a $TC_{50}$ of 12.83 μM, and had a SI of 1.7, 2.2, and 2.5, respectively. In Vero cell, Compound 3 also exhibited better activity (5.14 μM), and had a better SI than the positive control agent, and it could be seen that Compound 3 had a lower toxicity than the positive control agent.

TABLE 1-1

Results on anti-EV71 activity (therapeutic effect on Vero cell) of compounds of interest

| Compound No. | EV71 (SZ-98 strain) | | |
|---|---|---|---|
| | $TC_{50}$ (μmol/L) | $IC_{50}$ (μmol/L) | SI |
| Con 1 | 4.28 | >2.47 | — |
| 1 | 10.68 | 7.41 | 1.44 |
| 2 | 12.83 | >7.41 | — |
| 3 | 12.83 | 5.14 | 2.50 |
| 4 | 4.28 | >2.47 | — |
| 5 | 200 | >200 | — |
| 6 | 38.49 | >22.22 | — |
| 7 | 7.41 | >2.47 | — |
| 8 | 12.83 | >7.41 | — |
| 9 | 38.49 | >22.22 | — |
| 10 | 10.68 | >7.41 | — |
| 11 | 3.56 | >0.82 | — |
| 12 | 32.05 | >22.22 | — |
| 13 | 66.67 | >22.22 | — |
| 14 | 32.05 | 15.41 | 2.08 |

TABLE 1-2

Results on anti-EV71 activity (therapeutic effect on MRC-5 cell) of compounds of interest

| Compound No. | EV71 (SZ-98 strain) | | |
|---|---|---|---|
| | $TC_{50}$ (μmol/L) | $IC_{50}$ (μmol/L) | SI |
| Con 1 | 10.68 | >2.47 | — |
| 1 | 12.83 | >7.41 | — |
| 2 | 22.22 | >7.41 | — |
| 3 | 12.83 | >7.41 | — |
| 4 | 12.83 | >7.41 | — |
| 5 | >200 | >200 | — |
| 6 | 38.49 | >22.22 | — |
| 7 | 10.68 | >2.47 | — |
| 8 | 9.54 | >2.47 | — |
| 9 | 38.49 | >22.22 | — |
| 10 | 12.83 | >7.41 | — |
| 11 | 32.05 | >7.41 | — |
| 12 | 38.49 | >22.22 | — |
| 13 | 66.67 | >22.22 | — |
| 14 | 32.05 | 15.41 | 2.08 |

TABLE 1-3

Results on anti-EV71 activity (therapeutic effect on RD cell) of compounds of interest

| Compound No. | EV71 (SZ-98 strain) | | |
|---|---|---|---|
| | $TC_{50}$ (μmol/L) | $IC_{50}$ (μmol/L) | SI |
| Con 1 | 12.83 | 5.41 | 2.5 |
| 1 | 12.83 | >7.41 | — |
| 2 | 22.22 | >7.41 | — |
| 3 | 12.83 | 7.41 | 1.7 |
| 4 | 12.83 | 5.75 | 2.2 |
| 5 | >200 | 22.22 | 9.0 |
| 6 | 38.49 | 15.41 | 2.5 |
| 7 | 3.56 | >0.82 | — |
| 8 | 66.67 | 22.22 | 3.0 |
| 9 | 12.83 | >7.41 | — |
| 10 | 15.41 | >7.41 | — |
| 11 | 46.22 | >22.22 | — |
| 12 | 38.49 | >22.22 | — |
| 13 | 66.67 | >22.22 | — |
| 14 | 38.49 | 15.41 | 2.5 |

TABLE 2-1

Results on anti-EV71 activity (preventive effect on Vero cell) of compounds of interest

| Compound No. | EV71 (SZ-98 strain) | | |
|---|---|---|---|
| | $TC_{50}$ (μmol/L) | $IC_{50}$ (μmol/L) | SI |
| Con 1 | 4.28 | >2.47 | — |
| 1 | 10.68 | >7.41 | — |
| 2 | 12.83 | >7.41 | — |
| 3 | 12.83 | >7.41 | — |
| 4 | 4.28 | >2.47 | — |
| 5 | 200 | 22.22 | — |
| 6 | 38.49 | >22.22 | — |
| 7 | 7.41 | >2.47 | — |
| 8 | 12.83 | >7.41 | — |
| 9 | 38.49 | >22.22 | — |
| 10 | 10.68 | >7.41 | — |
| 11 | 3.56 | >0.82 | — |
| 12 | 32.05 | >22.22 | — |
| 13 | 66.67 | >22.22 | — |
| 14 | 32.05 | >22.22 | — |

TABLE 2-2

Results on anti-EV71 activity (preventive effect on RD cell) of compounds of interest

| Compound No. | EV71 (SZ-98 strain) | | |
|---|---|---|---|
| | $TC_{50}$ (μmol/L) | $IC_{50}$ (μmol/L) | SI |
| Con 1 | 12.83 | 5.14 | 2.5 |
| 1 | 12.83 | >7.41 | — |
| 2 | 22.22 | >7.41 | — |
| 3 | 12.83 | >7.41 | — |
| 4 | 12.83 | >7.41 | — |
| 5 | >200 | 200 | >1.0 |
| 6 | 38.49 | >22.22 | — |
| 7 | 3.56 | >0.82 | — |
| 8 | 66.67 | >22.22 | — |
| 9 | 12.83 | >7.41 | — |
| 10 | 15.41 | 5.14 | 3.0 |
| 11 | 46.22 | >22.22 | — |
| 12 | 38.49 | >22.22 | — |
| 13 | 66.67 | 7.41 | 9.0 |
| 14 | 38.49 | 22.22 | 1.7 |

Note:

in Table 1-1 to Table 1-3, Table 2-1 to Table 2-2, (1) "—" represents that a sample has no anti-viral activity at a maximal nontoxic dose; (2) $TC_{50}$: median toxic concentration; $IC_{50}$: half maximal inhibitory concentration; SI: selection index, SI = $TC_{50}/IC_{50}$.

15.2 Test Item: Evaluation on the Inhibitory Activity of a Compound on Clathrin-Mediated Endocytosis 1. Experiment principle: transferrin was a key protein for clathrin-mediated endocytosis. Therefore, by determining the effect of a compound on transferrin in HeLa cell, the inhibitory effect of the compound on clathrin-mediated endocytosis could be evaluated.

2. Sample treatment: a test compound was dissolved in DMSO to prepare a stock solution, which was stored at −20° C. The stock solution was diluted with HEPES buffer (25 mm HEPES, 20 mm Glucose, 1% BSA, sterile water) to prepare a solution with an initial concentration of 40 mM before use, and was 2-fold diluted with the buffer to obtain 6 diluted concentrations from 1.25 to 40 μmol/L.

4. Test method: HeLa cells (provided by the Cell Bank of Chinese Academy of Sciences) were seeded on a 24-well culture plate coated with 0.1 mg/ml polylysine, a serum-free medium DMEM (Gibco Company) was added at 500

μl/well, and the cells were cultured for one night. To each well, 0.5 μl a test compound at a different diluted concentration or 0.1 v/v % DMSO was added, then the pretreatment was performed for 15 min, and then 20 μg/ml alexa$^{568}$ transferrin (2 μl) (TF, SIGMA-ALDRICH Company) was added, and the incubation was carried out at 37° C. for 15 min. The resultant mixture was then washed with Live Cell Imaging Solution (LCIS, Invitrogen Company) and an acid at a low pH (0.5 μM NaCl solution containing 0.5% acetic acid) for 30 s, respectively, followed by fixing with cold methanol, and was observed under fluorescence microscope.

5. Experimental result

Five compounds including Compounds 3, 10, 13, 14 and pitstop2 (Con1) were tested for their effects on endocytosis of transferrin in HeLa cells. When HeLa cells were exposed to Alexa$^{568}$ transferrin, they could effectively endocytose transferrin, and transferrin was distributed perinuclearly. Compounds 3, 10, 14 and pitstop2 exhibited the inhibitory effect on endocytosis of transferrin, which was dose-dependent. When 20 μM Compound 3, 10, or 14 was added to cells, the endocytosis of transferrin was completely inhibited in HeLa cells, and the inhibition rate was shown in Table 3.

TABLE 3

Inhibitory effect of 20 μM compound on clathrin-mediated endocytosis of transferrin

| Compound No. | Inhibition rate |
| --- | --- |
| 3 | 100% |
| 10 | 100% |
| 13 | 50% |
| 14 | 100% |
| Con1 | 50% |

What is claimed is:

1. A compound represented by Formula Ic or Formula Id, a racemate or an optical isomer thereof, or a pharmaceutically acceptable salt, a solvate or a hydrate thereof

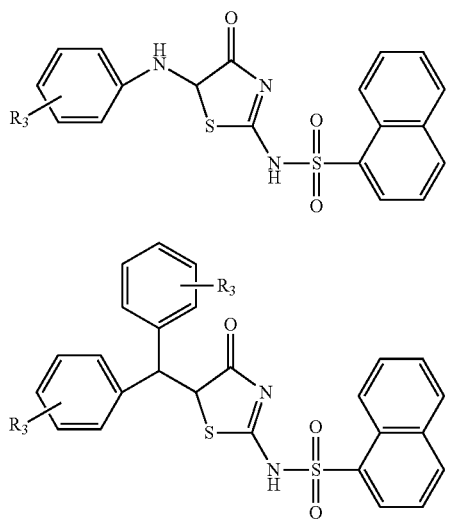

wherein, $R_3$ represents 1, 2, 3 or 4 identical or different substituents present on the phenyl ring, each $R_3$ is independently selected from the group consisting of: hydrogen, halogen, hydroxyl, $C_{1-8}$ alkyl, $C_{1-8}$ haloalkyl, $C_{1-8}$ alkoxy, amino, amino monosubstituted or disubstituted with $C_{1-8}$ alkyl, carboxyl, R'(C=O)NH—, and phenyl, wherein R' is $C_{1-8}$ alkyl.

2. The compound according to claim 1, racemate or an optical isomer thereof, or a pharmaceutically acceptable salt, a solvate or a hydrate thereof, wherein, $R_3$ represents 1, 2, or 3 identical or different substituents present on the phenyl ring, each $R_3$ is independently selected from the group consisting of: hydrogen, halogen, hydroxyl, $C_{1-6}$ alkyl, $C_{1-6}$ haloalkyl, $C_{1-6}$ alkoxy, amino, amino monosubstituted or disubstituted with $C_{1-6}$ alkyl, carboxyl, R'(C=O)NH—, and phenyl, wherein R' is $C_{1-6}$ alkyl.

3. The compound according claim 1, a racemate or an optical isomer thereof, or a pharmaceutically acceptable salt, a solvate or a hydrate thereof, which is selected from the group consisting of:

Naphthalene-1-sulfonic acid (4-oxo-5-phenylamino-4,5-dihydro-thiazol-2-yl) amide (Compound 13), and Naphthalene-1-sulfonic acid {5-[(4-bromo-phenyl)-phenyl-methyl]-4-oxo-4,5-dihydro-thiazol-2-yl} amide (Compound 14).

4. A pharmaceutical composition, comprising at least one compound according to claim 1, a racemate or an optical isomer thereof, or a pharmaceutically acceptable salt, a solvate or a hydrate thereof, and one or more pharmaceutically acceptable carriers or excipients.

5. A method for treatment of a viral infection caused by EV71, comprising administering to a subject in need thereof a therapeutically effective amount of at least one compound according to claim 1, a racemate or an optical isomer thereof, or a pharmaceutically acceptable salt, a solvate or a hydrate thereof.

6. A method for treatment of hand-foot-mouth disease, comprising administering to a subject in need thereof a therapeutically effective amount of at least one compound according to claim 1, a racemate or an optical isomer thereof, or a pharmaceutically acceptable salt, a solvate or a hydrate thereof.

7. The compound according to claim 2, a racemate or an optical isomer thereof, or a pharmaceutically acceptable salt, a solvate or a hydrate thereof, wherein $R_3$ represents 1 or 2 identical or different substituents present on the phenyl ring, each $R_3$ is independently selected from the group consisting of: hydrogen, halogen, hydroxyl, $C_{1-4}$ alkyl, $C_{1-4}$ haloalkyl, $C_{1-4}$ alkoxy, amino, amino monosubstituted or disubstituted with $C_{1-4}$ alkyl, carboxyl, R'(C=O)NH—, and phenyl, wherein R' is $C_{1-4}$ alkyl.

8. The compound according to claim 2, a racemate or an optical isomer thereof, or a pharmaceutically acceptable salt, a solvate or a hydrate thereof, wherein $R_3$ represents 1 or 2 identical or different substituents present on the phenyl ring, each $R_3$ is independently selected from the group consisting of: hydrogen, fluorine, chlorine, bromine, hydroxyl, methyl, ethyl, n-propyl, isopropyl, n-butyl, isobutyl, sec-butyl, tert-butyl, trifluoromethyl, methoxy, ethoxy, propoxy, amino, methylamino, dimethylamino, ethylamino, diethylamino, propylamino, carboxyl, $CH_3(C=O)NH$—, $C_2H_5(C=O)NH$—, and phenyl.

9. The compound according to claim 2, racemate or an optical isomer thereof, or a pharmaceutically acceptable salt, a solvate or a hydrate thereof, wherein $R_3$ represents 1 or 2 identical or different substituents present on the phenyl ring, each $R_3$ is independently selected from the group consisting of: hydrogen, fluorine, chlorine, bromine, hydroxyl, methoxy, amino, diethylamino, propylamino, carboxyl, $CH_3(C=O)NH$—, and phenyl.

10. A compound, a racemate or an optical isomer thereof, or a pharmaceutically acceptable salt, a solvate or a hydrate thereof, which is selected from the group consisting of:

Naphthalene-1-sulfonic acid [5-(3-methoxy-4-hydroxy-benzylidene)-4-oxo-4,5-dihydro-thiazol-2-yl] amide (Compound 2), Naphthalene-1-sulfonic acid [5-(2-hydroxy-4-diethylamino-benzylidene)-4-oxo-4,5-dihydro-thiazol-2-yl] amide (Compound 3), Naphthalene-1-sulfonic acid [5-(4-chloro-benzylidene)-4-oxo-4,5-dihydro-thiazol-2-yl] amide (Compound 4), Naphthalene-1-sulfonic acid [5-(4-carboxy-benzylidene)-4-oxo-4,5-dihydro-thiazol-2-yl] amide (Compound 5), Naphthalene-1-sulfonic acid [5-(3-hydroxy-benzylidene)-4-oxo-4,5-dihydro-thiazol-2-yl] amide (Compound 6), Naphthalene-1-sulfonic acid [5-(3-hydroxy-4-methoxy-benzylidene)-4-oxo-4,5-dihydro-thiazol-2-yl] amide (Compound 7), Naphthalene-1-sulfonic acid [5-(3-bromo-4-hydroxy-benzylidene)-4-oxo-4,5-dihydro-thiazol-2-yl] amide (Compound 8), Naphthalene-1-sulfonic acid [5-(2,6-dimethoxy-benzylidene)-4-oxo-4,5-dihydro-thiazol-2-yl] amide (Compound 9), Naphthalene-1-sulfonic acid [5-(2-chloro-4-fluoro-benzylidene)-4-oxo-4,5-dihydro-thiazol-2-yl] amide (Compound 10), Naphthalene-1-sulfonic acid (5-biphenyl-4-yl-methylene-4-oxo-4,5-dihydro-thiazol-2-yl) amide (Compound 11), and Naphthalene-1-sulfonic acid [5-(4-acetylamino-benzylidene)-4-oxo-4,5-dihydro-thiazol-2-yl] amide (Compound 12).

11. A pharmaceutical composition, comprising at least one compound according to claim 10, a racemate or an optical isomer thereof, or a pharmaceutically acceptable salt, a solvate or a hydrate thereof, and one or more pharmaceutically acceptable carriers or excipients.

12. A method for treatment of a viral infection caused by EV71, comprising administering to a subject in need thereof a therapeutically effective amount of at least one compound according to claim 10, a racemate or an optical isomer thereof, or a pharmaceutically acceptable salt, a solvate or a hydrate thereof.

13. A method for treatment of hand-foot-mouth disease, comprising administering to a subject in need thereof a therapeutically effective amount of at least one compound according to claim 10, a racemate or an optical isomer thereof, or a pharmaceutically acceptable salt, a solvate or a hydrate thereof.

* * * * *